United States Patent [19]

Isogai et al.

[11] 4,332,966
[45] Jun. 1, 1982

[54] PROCESS FOR PRODUCING 3-PENTENOIC ESTERS

[75] Inventors: Nobuo Isogai; Motoyuki Hosokawa; Takashi Okawa; Natuko Wakui; Toshiyasu Watanabe, all of Niigata, Japan

[73] Assignee: Mitsubishi Gas Chemical Company, Inc., Tokyo, Japan

[21] Appl. No.: 199,332

[22] Filed: Oct. 21, 1980

[30] Foreign Application Priority Data

Dec. 17, 1979 [JP] Japan .............................. 54/163840
Sep. 8, 1980 [JP] Japan .............................. 55/124255

[51] Int. Cl.$^3$ ............................................. C07C 67/36
[52] U.S. Cl. .................................................... 560/206
[58] Field of Search ............................... 560/206, 207

[56] References Cited

U.S. PATENT DOCUMENTS 2,882,299 4/1959 Smolin et al. ...................... 560/206
3,778,466 12/1973 Matsuda .............................. 560/206

FOREIGN PATENT DOCUMENTS 2630086 1/1978 Fed. Rep. of Germany .
49-10935 3/1974 Japan .

OTHER PUBLICATIONS

Matsuda, A. "The Cobalt Carbonyl-catalyzed Hydroesterification of Butadiene with Carbon Monoxide and Methanol", Bulletin of the Chemical Society of Japan, vol. 46, 524–530 (1973).

Primary Examiner—Alan Siegel
Attorney, Agent, or Firm—Browdy and Neimark

[57] ABSTRACT

A process is disclosed for producing a 3-pentenoic ester which comprises reacting butadiene, carbon monoxide and an alcohol in the presence of cobalt carbonyl catalyst, characterized in that the reaction is carried out in a reaction medium composed of at least two solvents selected from the group consisting of pyridine, quinoline, isoquinoline and substituted pyridine, substituted quinoline and substituted isoquinoline in which substituent or substituents are selected from the group consisting of alkyl having 1–6 carbon atoms, alkenyl having 1–6 carbon atoms, aryl, alkylaryl having 7–10 carbon atoms and aralkyl having 7–10 carbon atoms.

11 Claims, No Drawings

PROCESS FOR PRODUCING 3-PENTENOIC ESTERS

BACKGROUND OF THE INVENTION

This invention relates to a process for producing a 3-pentenoic ester through hydroesterification reaction of butadiene on an industrial scale, and particularly relates to a process for producing a 3-pentenoic ester which comprises hydroesterification of butadiene in the presence of cobalt carbonyl catalyst, characterized by using a reaction medium composed of at least two solvents selected from compounds having pyridine ring, compounds having quinoline ring and compounds having isoquinoline ring.

Many processes for producing 3-pentenoic esters in which butadiene, an alcohol and carbon monoxide are reacted are known to those skilled in the art. For example, a process for producing a 3-pentenoic ester which comprises reacting butadiene, an alcohol and carbon monoxide in the presence of dicobalt octacarbonyl as a catalyst and a tertiary amine as a solvent and a process for producing a 3-pentenoic ester which comprises reacting butadiene, an alcohol and carbon monoxide in the presence of cobalt carbonyl complex synthesized from cobalt carbonyl and a tertiary amine are known from Bulletin of the Chemical Society of Japan vol. 46 (1973) 524–530 pages. However, according to the above processes 3-pentenoic esters as well as by-products, such as 4-vinyl-1-cyclohexene, dibutyl ketone, methylglutarate and high boiling materials derived from polymerization of butadiene are formed. Therefore, selectivity to a 3-pentenoic ester becomes low. Japanese Patent Publication No. 10935/1974 discloses a process for producing a 3-pentenoic ester which comprises hydroesterificating butadiene in the presence of cobalt carbonyl as a catalyst and pyridine as a solvent. However, a large amount of expensive cobalt carbonyl has to be used in order to increase yield of the 3-pentenoic ester according to this process; that is, cobalt carbonyl is required in order to selectively control hydroesterification reaction of butadiene and prevent forming of high boiling materials derived from polymerization of butadiene and other by-products.

In the working examples of Patent Publication No. 10935/1974, the amount of cobalt carbonyl catalyst used is 0.04 moles per 1 mole of butadiene. However, we found that when either one of pyridine or isoquinoline is used as a solvent, more than 0.1 mole of dicobalt carbonyl compound is necessary per 1 mole of butadiene. Even when a large amount of cobalt carbonyl catalyst is used, the invention of Patent Publication No. 10935/1974 results in forming by-products, such as 4-vinyl-1-cyclohexene, dibutyl ketone, methyl glutarate, high boiling materials derived from polymerization of butadiene and the like. Therefore, the yield of 3-pentenoic ester and selectivity to 3-pentenoic ester according to the process of Patent Publication No. 10935/1974 are not necessarily satisfactory. One of the most important factors in practicing the process industrially is how to recover the expensive catalyst effectively. The prior methods for recovering the catalyst are costly. So, at present in case of producing a 3-pentenoic ester from butadiene the main point of interest is how to reduce the amount of catalyst employed.

SUMMARY OF THE INVENTION

The present inventors carried out research on a process for producing a 3-pentenoic ester by hydroesterification reaction of butadiene in a high yield and with a high selectivity; that is, research was directed to enhancing the catalyst activity in such process. As a result, we found a process for producing a 3-pentenoic ester in high yield and with high selectivity with a small amount of catalyst.

Therefore, one object of this invention is to provide a process for producing a 3-pentenoic ester by hydroesterification reaction of butadiene using less cobalt carbonyl catalyst than is used in the prior method.

Another object of this invention is to provide a process for producing a 3-pentenoic ester in high yield and with high selectivity in which little of the by-products, such as 4-vinyl-1-cyclohexene, dibutyl ketone, methyl glutarate, high boiling materials derived from polymerization of butadiene, and the like is formed.

This invention relates to a process for producing a 3-pentenoic ester which comprises reacting butadiene, carbon monoxide and an alcohol in the presence of cobalt carbonyl catalyst, characterized in that the reaction is carried out in a reaction medium composed of at least two solvents selected from the group consisting of pyridine, quinoline, isoquinoline and substituted pyridine, substituted quinoline and substituted isoquinoline in which substituent or substituents are selected from the group consisting of alkyl having 1–6 carbon atoms, alkenyl having 1–6 carbon atoms, aryl, alkylaryl having 7–10 carbon atoms and aralkyl having 7–10 carbon atoms.

DETAILED DESCRIPTION OF THE INVENTION

The solvents employed in the practice of this invention are N-heterocyclic compounds including pyridine, α-picoline, β-picoline, γ-picoline, 2,3-lutidine, 2,4-lutidine, 2,5-lutidine, 2,6-lutidine, 3,4-lutidine, 3,5-lutidine, 4-benzyl pyridine, 4-vinyl pyridine, quinoline and isoquinoline. Of these compounds, pyridine, β-picoline, γ-picoline, 3,4-lutidine, 3,5-lutidine and isoquinoline are preferred.

It is critical that at least two solvents as mentioned above be used. In general, any one of at least two solvents is preferably used in an amount of more than 2 moles %, more preferably 5 moles %, most preferably 10 moles % on the basis of total mole of the solvents. The use of mixture of the solvents in which any one of the solvents is present in an amount of more than 2 moles % gives results superior to those obtained with the use of one solvent.

The amount of mixture of the solvents employed is not critical. In general, the mixture of the solvents is used in an amount of from 0.05 to 10% by weight on the basis of weight of butadiene, preferably from 0.2 to 3% by weight. Use of the mixed solvents in an amount less than 0.05% by weight is likely to cause side-reaction. The mixed solvents in an amount of more than 10% by weight lowers the reaction speed and increases the cost of recovering the solvents.

The cobalt carbonyl catalyst employed in the practice of this invention include cobalt carbonyl and cobalt carbonyl complex.

The cobalt carbonyl catalyst may be the synthetic solution obtained by reacting synthetic gas (CO and $H_2$) with cobalt compound(s) selected from the group consisting of inorganic cobalt compounds, such as cobalt hydroxide, cobalt carbonate and basic cobalt carbonate or organic cobalt compounds, such as cobalt organic acid salts, cobaltocene and cobalt acetylacetonate in the alcohol employed as a starting material, and the synthetic solution obtained by reacting the cobalt compound(s), said N-heterocyclic compound or other compound having ligand, and CO gas.

In the prior method for producing a 3-pentenoic ester by hydroesterificating butadiene by using a large amount of cobalt carbonyl or cobalt carbonyl complex, the cobalt carbonyl or the cobalt carbonyl complex must be prepared by a complicated and costly process. On the other hand, since a 3-pentenoic ester can be prepared by using a small amount of catalyst according to the present invention, the synthetic solution containing cobalt carbonyl catalyst can be prepared easily from an inorganic or organic cobalt compound.

The amount of cobalt carbonyl catalyst employed is not critical. When dicobalt octacarbonyl is employed, preferably, dicobalt octacarbonyl in an amount of 0.001 to 0.05 moles per 1 mole of butadiene, more preferably dicobalt octacarbonyl in an amount of 0.005 to 0.03 moles may be industrially practiced. The use of catalyst in an amount of less than the lower limit as mentioned above lowers the reaction speed too much. The use of catalyst in an amount of more than the upper limit merely adds to production cost, since the cost of recovering the catalyst increases.

In the present invention, a specified polymerization inhibitor may be added to the reaction system. Addition of the polymerization inhibitor to the reaction system increases yield of the object product and selectivity to the object product without retarding the reaction speed.

The polymerization inhibitors employed in the practice of this invention are inhibitors for vinyl polymerization. The compounds which are known as an inhibitor for vinyl polymerization are amino compounds, quinone compounds, hydroxy compounds, nitro compounds, nitroso compounds, sulfur compounds, organic sulfur compounds and inorganic salts. However, of these inhibitors, only aromatic amino compounds, quinone compounds and aromatic hydroxy compounds (except hydroquinone) can be employed as a polymerization inhibitor of this invention. Examples of the aromatic amino compounds include N-methylaniline, diphenylamine, N,N'-tetraethyl-p-phenylenediamine, N,N'-di-$\beta$-naphthyl-p-phenylenediamine. Examples of quinone compounds include p-benzoquinone, chloranil, anthraquinone and phenanthraquinone.

Examples of the hydroxy compounds include catechol and its derivatives, such as p-tert.-butylcatechol. One of the polymerization inhibitors or mixtures thereof may be used in the present invention. The amount of the polymerization inhibitor employed may be more than 0.0001 mole per 1 mole of butadiene. The upper limit of the amount if unnecessary to be specified. In general, the use of the polymerization inhibitor in an amount of less than 0.1 mole % is sufficiently effective. The use of the inhibitor in an amount of more than 0.1 mole merely adds to production cost. However, compounds which are liquid at room temperature and have relatively low melting point, for example, N-methyl aniline and diphenylamine in an amount of less than 10 moles, preferably less than 5 mole per 1 mole of butadiene may be used as a solvent in combination with the reaction medium compound of at least two solvents as mentioned above. The use of the compound, such as N-methyl aniline or diphenylamine can reduce the amount of an expensive tertiary amine employed.

Alcohols employed in the practice of this invention include alcohols having 1–10 carbon atoms, such as methanol, ethanol, propanol and butanol. Methanol and ethanol are important industrially. One of these alcohols or mixture thereof may be used. The amount of the alcohol employed is not critical. Preferably, the alcohol in an amount of more than equivalent mole to butadiene, more preferably the alcohol in an amount of 1 to 5 moles per 1 mole of butadiene may be used. When the alcohol in an amount of less than equivalent mole to butadiene is used, expensive butadiene is consumed for undesirable side reaction. The use of the alcohol in an amount of more than 5 moles per mole of butadiene lowers the hydroesterification reaction speed.

The reaction temperature is not critical. Profitably, the reaction temperature may be in the range of 80° to 200° C., preferably 100° to 140° C. Partial pressure of carbon monoxide is not critical. Preferably, partial pressure of carbon monoxide may be more than 50 Kg/cm$^2$, and the partial pressure in the range of 100 to 400 Kg/cm$^2$.

When the hydroesterification reaction of butadiene is carried out in a reaction medium composed of at least two N-heterocyclic compounds, the reaction speed is sufficiently fast, even if only a small amount of cobalt carbonyl catalyst is used, and the undesirable side reaction is sufficiently suppressed.

According to the present invention, hydroesterification reaction of butadiene can be effected with little expenditure for catalyst.

The present invention can be carried out either as batch process or as a continuous process.

The present invention is further illustrated by nonlimiting Examples.

EXAMPLES 1 and 2

Into a 200 ml stainless steel autoclave equipped with magnet stirrer were charged 15 grs. (0.277 moles) of butadiene, 11 grs. (0.343 moles) of methanol and dicobalt octacarbonyl catalyst and pyridine-isoquinoline mixture in an amount as given in Table 1. The reaction was effected at 122° C. under carbon monoxide partial pressure of 300 Kg/cm$^2$. The results are shown in Table 1.

CONTROL TESTS 1–6

Control tests 1–3 correspond to Example 1 and control tests 4–6 correspond to Example 2. The reaction conditions are shown in Table 1. The results are also shown in Table 1.

When the reaction was effected in pyridine alone or isoquinoline alone, the reaction speed is slow and yield of methyl 3-pentenoate and selectivity to methyl 3-pentenoate are very low.

TABLE 1

| Examples and Control tests | | Example 1 | Control test 1 | Control test 2 | Control test 3 | Example 2 | Control test 4 | Control test 5 | Control test 6 |
|---|---|---|---|---|---|---|---|---|---|
| components | butadiene g (mole) | 15(0.277) | | | | 15(0.277) | | | |
| | methanol g (mole) | 11(0.343) | same as | same as | same as | 11(0.343) | same as | same as | same as |

TABLE 1-continued

| Examples and Control tests | | Example 1 | Control test 1 | Control test 2 | Control test 3 | Example 2 | Control test 4 | Control test 5 | Control test 6 |
|---|---|---|---|---|---|---|---|---|---|
| conditions | $Co_2(CO)_8$ g (mole) | 2(0.0058) | the left | the left | the left | 0.9(0.0026) | the left | the left | the left |
| | pyridine g (mole) | 10(0.126) | 10(0.126) | — | — | 10(0.126) | 10(0.126) | 20(0.253) | — |
| | isoquinoline g (mole) | 10(0.077) | — | 10(0.077) | 20(0.155) | 10(0.077) | — | — | 20(0.155) |
| | reaction temp. (°C.) | 122 | same as the left | same as the left | same as the left | 125 | same as the left | same as the left | same as the left |
| | reaction pressure (°C.) | 300 | the left | the left | the left | 300 | the left | the left | the left |
| | reaction time (hr) | 1.8 | 2.5 | 2.5 | 3.5 | 3.0 | 3.5 | 5.0 | 3.5 |
| Reactivity of butadiene mole % | | 93.5 | 79.0 | 80.8 | 94.0 | 92.6 | 62.1 | 91.0 | 57.4 |
| Yield of methyl 3-pentenoate mole % | | 84.7 | 48.2 | 61.5 | 58.9 | 83.3 | 28.9 | 37.2 | 30.4 |
| Selectivity to methyl 3-pentenoate mole % | | 90.6 | 61.0 | 76.1 | 62.7 | 90.0 | 46.5 | 40.9 | 53.0 |
| Selectivity to methyl 2 or 4 pentenoate mole % | | 3.9 | 1.1 | 1.5 | 1.2 | 3.1 | 0.2 | 0.3 | 1.1 |
| Selectivity to 4-vinyl-1-cyclohexene mole % | | 3.8 | 7.9 | 5.2 | 5.0 | 3.7 | 10.6 | 14.5 | 11.8 |
| Selectivity to dibutyl ketone mole % | | 1.4 | 2.6 | 2.3 | 1.3 | 1.1 | 1.3 | 1.2 | 1.1 |
| Selectivity to dimethyl methylglutarate mole % | | 0.2 | 2.0 | 1.2 | 1.0 | 0.2 | 0.6 | 0.4 | 0.7 |
| Selectivity to other unknown components containing polymers mole % | | 0.2 | 25.4 | 13.6 | 28.8 | 2.0 | 40.8 | 42.7 | 32.4 |

Note:
Yield and selectivity were calculated on the basis of butadiene in Table 1–5.

EXAMPLES 3 and 4

The procedures of Example 1 were repeated except that the proportion of the mixed solvents as given in Table 2 was used. The results are shown in Table 2.

TABLE 2

| | Example No. | Example 3 | Example 4 |
|---|---|---|---|
| Component | butadiene g (mole) | 15(0.277) | 15(0.277) |
| | methanol g (mole) | 11(0.343) | 11(0.343) |
| | $Co_2(CO)_8$ g (mole) | 2(0.0058) | 2(0.0058) |
| | pyridine g (mole) | 10(0.126) | 0.6(0.008) |
| | isoquinoline g (mole) | 1.5(0.012) | 10(0.077) |
| Conditions | reaction temperature (°C.) | 122 | 122 |
| | reaction pressure of CO(kg/cm²) | 300 | 300 |
| | reaction time (hr) | 2.0 | 2.0 |
| Reactivity of butadiene mole % | | 93.9 | 92.0 |
| Yield of methyl 3-pentenoate mole % | | 82.5 | 79.7 |
| Selectivity to methyl 3-pentenoate mole % | | 87.9 | 86.6 |
| Selectivity to methyl 2 or 4 pentenoate mole % | | 2.2 | 1.6 |
| Selectivity to 4-vinyl-1-cyclohexene mole % | | 4.1 | 4.7 |
| Selectivity to dibutyl ketone mole % | | 1.8 | 1.6 |
| Selectivity to dimethyl methylglutarate mole % | | 1.6 | 1.0 |
| Selectivity to other unknown components containing polymers mole % | | 2.4 | 4.6 |

EXAMPLES 5–9 AND CONTROL TESTS 7–10

The reactions were effected under the conditions as given in Table 3. The results are shown in Table 3.

TABLE 3

| Examples and Control tests | | Exampl 5 | Control test 7 | Exampl 6 | Control test 8 | Exampl 7 | Control test 9 | Exampl 8 | Exampl 9 | Control test 10 |
|---|---|---|---|---|---|---|---|---|---|---|
| components | butadiene g (mole) | 15(0.277) | | | | | | | 15(0.277) | |
| | methanol g (mole) | 11(0.343) | same as the left | same as the left | same as the left | same as the left | same as the left | same as the left | 11(0.343) | same as the left |
| | $Co_2(CO)_8$ g (mole) | 2(0.0058) | | | | | | | 2(0.0058) | |
| | Solvent I  kind | pyridine | — | pyridine | — | pyridine | — | γ-picoline | pyridine | — |
| |             g | 10(0.126) | | 10(0.126) | | 10(0.126) | | 10(0.107) | 10(0.126) | |
| | Solvent II  kind | γ-picoline | same as the left | β-picoline | same as the left | 3,5-lutidine | same as the left | β-picoline | 3,4-lutidine | same as the left |
| |             g | 10(0.107) | | 10(0.107) | | 10(0.093) | | 10(0.107) | 10(0.093) | |
| condition | reaction temp. °C. | 122 | 122 | 122 | 122 | 122 | 122 | 122 | 122 | 122 |
| | reaction pressure (CO) Kg/cm² | 300 | 300 | 300 | 300 | 300 | 300 | 300 | 300 | 300 |
| | reaction time hr | 1.5 | 2.5 | 1.5 | 2.5 | 1.5 | 2.5 | 1.5 | 1.5 | 2.5 |
| Reactivity of butadiene mole % | | 99.3 | 97.3 | 99.0 | 96.7 | 95.2 | 80.5 | 98.1 | 96.9 | 85.4 |
| Yield of methyl 3-pentenoate mole % | | 90.8 | 75.3 | 92.6 | 76.3 | 85.1 | 52.6 | 89.1 | 87.7 | 56.7 |
| Selectivity to methyl 3-pentenoate mole % | | 91.0 | 77.4 | 93.5 | 78.9 | 89.4 | 65.3 | 90.8 | 90.5 | 66.4 |
| Selectivity to methyl 2 or 4 pentenoate mole % | | 2.0 | 0.5 | 1.3 | 0.4 | 2.1 | 1.2 | 1.5 | 2.0 | 1.3 |
| Selectivity to 4-vinyl-1-cyclohexene mole % | | 3.4 | 5.7 | 3.5 | 6.2 | 4.0 | 7.4 | 3.7 | 3.9 | 6.7 |
| Selectivity to dibutyl ketone mole % | | 0.7 | 1.1 | 0.8 | 2.0 | 1.2 | 2.2 | 1.0 | 1.0 | 2.4 |
| Selectivity to dimethyl | | | | | | | | | | |

TABLE 3-continued

| Examples and Control tests | Exampl 5 | Control test 7 | Exampl 6 | Control test 8 | Exampl 7 | Control test 9 | Exampl 8 | Exampl 9 | Control test 10 |
|---|---|---|---|---|---|---|---|---|---|
| methylglutarate mole % | 0.3 | 1.3 | 0.4 | 1.5 | 0.5 | 1.3 | 0.5 | 0.4 | 1.8 |
| Selectivity to other unknown components containing polymers mole % | 2.6 | 14.0 | 0.5 | 11.0 | 2.8 | 22.6 | 2.5 | 2.2 | 21.4 |

EXAMPLE 10

Into a 500 ml stainless steel autoclave equipped with magnet stirrer were charged 56 grs. (1.035 mole) of butadiene, 63 grs. (1.367 mole) of ethanol and dicobalt octacarbonyl catalyst and pyridine-isoquinoline in an amount as given in Table 4. The reaction was effected at 123° C. under carbon monoxide partial pressure of 300 Kg/cm². The conditions are shown in Table 4.

CONTROL TESTS 11 AND 12

Control tests 11 and 12 corresponding to Example 10 are shown in Table 4. When the reaction was effected in pyridine alone or isoquinoline alone, the reaction speed was slow and yield of ethyl 3-pentenoate and selectivity to ethyl 3-pentenoate were very low.

TABLE 4

| | Example No. or Control test No. | Example 10 | Control test 11 | Control test 12 |
|---|---|---|---|---|
| components | butadiene g (mole) | 56(1.035) | same as the left | same as the left |
| | ethanol g (mole) | 63(1.367) | | |
| | Co₂(CO)₈ g (mole) | 7(0.0205) | | |
| | pyridine g (mole) | 40(0.506) | 40(0.506) | |
| | isoquinoline g (mole) | 40(0.294) | | 40(0.506) |
| reaction condition | reaction temperature °C. | 123 | same as the left | same as the left |
| | reaction pressure (CO) Kg/cm² | 300 | | |
| | reaction time hr | 2.5 | 4.0 | 4.0 |
| Reactivity of butadiene mole % | | 96.4 | 78.6 | 82.0 |
| Yield of ethyl 3-pentenoate mole % | | 88.2 | 42.4 | 48.0 |
| Selectivity of ethyl 3-pentenoate mole % | | 91.5 | 54.0 | 58.5 |
| Selectivity to ethyl 2- or 4-pentenoate mole % | | 2.0 | 1.5 | 1.8 |
| Selectivity to 4-vinyl-1-cyclohexene mole % | | 0.4 | 6.3 | 5.9 |
| Selectivity to dibutyl ketone mole % | | 0.5 | 3.0 | 2.6 |
| Selectivity to diethyl methylglutarate mole % | | 0.1 | 2.7 | 2.5 |
| Selectivity to other unknown components containing polymers mole % | | 5.2 | 32.5 | 28.7 |

EXAMPLES 11-24

Into a 200 ml stainless steel autoclave equipped with magnet stirrer 15 grs. (0.277 mole) of butadiene, 11 grs. (0.343 mole) of methanol and 2 grs. of dicobalt octacarbonyl and solvent and polymerization inhibitor in an amount as given in Table 5 were charged. The reactions were effected at 120° C. under 300 Kg/cm²G.

The results are shown in Table 5.

TABLE 5

| Examples and Control tests | | Example 11 | Example 12 | Example 13 | Example 14 | Example 15 | Example 16 | Example 17 |
|---|---|---|---|---|---|---|---|---|
| component | | | | | | | | |
| butadiene g (mole) | | 15(0.277) | same as the left | same as the left | same as the left | 15(0.277) | same as the left | 15(0.277) |
| methanol g (mole) | | 11(0.343) | | | | 11(0.343) | | 11(0.343) |
| Co₂(CO)₈ g (mole) | | 2(0.0058) | | | | 2(0.0058) | | 2(0.0058) |
| solvent I | kind | pyridine | | | | pyridine | | pyridine |
| | g (mole) | 10(0.126) | | | | 10(0.126) | | 10(0.126) |
| solvent II | kind | isoquinoline | | | | β-picoline | | γ-picoline |
| | g (mole) | 10(0.077) | | | | 10(0.107) | | 10(0.107) |
| polymerization inhibitor | kind | diphenylamine | N,N'-di-β-naphthyl p-phenylenediamine | t-butyl catechol | p-benzoquinone | same as Ex. 11 | same as Ex. 12 | diphenyl amine |
| | g (mole) | 1.0(0.006) | 1.0(0.003) | 1.0(0.006) | 1(0.010) | 1.0(0.006) | 1.0(0.003) | 1.0(0.006) |
| condition | | | | | | | | |
| reaction temperature °C. | | 122 | same as the left | same as the left | same as the left | same as the left | same as the left | 122 |
| reaction pressure (CO) Kg/cm² | | 300 | | | | | | 300 |
| reaction time hr | | 2.0 | 2.0 | 2.0 | 2.0 | 1.5 | 1.5 | 1.5 |
| Reactivity of butadiene mole % | | 93.4 | 94.7 | 94.3 | 92.1 | 99.3 | 99.5 | 98.4 |
| Yield of methyl 3-pentenoate mole % | | 91.2 | 92.8 | 91.5 | 89.1 | 97.5 | 98.0 | 96.4 |
| Selectivity to methyl 3-pentenoate mole % | | 97.6 | 98.0 | 97.1 | 96.7 | 98.2 | 98.5 | 98.0 |
| Selectivity to methyl 2 or 4 pentenoate mole % | | 0.3 | 0.2 | 0.4 | 0.3 | 0.2 | 0.2 | 0.2 |
| Selectivity to 4-vinyl-1-cyclohexene mole % | | 1.4 | 1.3 | 1.4 | 1.5 | 1.2 | 1.0 | 1.1 |
| Selectivity to dibutyl ketone mole % | | 0.2 | 0.1 | 0.2 | 0.3 | 0.1 | 0.1 | 0.1 |

TABLE 5-continued

| | | | | | | | |
|---|---|---|---|---|---|---|---|
| Selectivity to dimethyl methylgultarate mole % | <0.1 | 0.1 | 0.1 | <0.1 | <0.1 | <0.1 | <0.1 |
| Selectivity to other unknown components containing polymers mole % | 0.4 | 0.3 | 0.8 | 1.1 | 0.2 | 0.2 | 0.5 |
| Examples and Control tests | Example 18 | Example 19 | Example 20 | Example 21 | Example 22 | Example 23 | Example 24 |
| component | | | | | | | |
| butadiene g (mole) | 15(0.277) | 15(0.277) | same as the left | 15(0.277) | same as the left | 15(0.277) | same as the left |
| methanol g (mole) | 11(0.343) | 11(0.343) | | 11(0.343) | | 11(0.343) | |
| Co$_2$(CO)$_8$ g (mole) | 2(0.0058) | 2(0.0058) | | 2(0.0058) | | 2(0.0058) | |
| solvent I    kind | pyridine | pyridine | | pyridine | | β-picoline | |
| g (mole) | 10(0.126) | 10(0.126) | | 10(0.126) | | 10(0.107) | |
| solvent II   kind | γ-picoline | 3,4-lutidine | | 3,5-lutidine | | γ-picoline | |
| g (mole) | 10(0.107) | 10(0.093) | | 10(0.093) | | 10(0.107) | |
| polymerization inhibitor   kind | t-butyl catechol | diphenyl amine | N,N'-di-β-naphthyl p-phenylene diamine | diphenyl amine | p-benzoquinone | diphenyl amine | N,N'-di-β-naphthyl p-phenylene diamine |
| g (mole) | 1.0(0.006) | 1.0(0.006) | 1.0(0.003) | 1.0(0.006) | 1.0(0.010) | 1.0(0.006) | 1.0(0.003) |
| condition | | | | | | | |
| reaction temperature °C. | 122 | same as the left | same as the left | same as the left | same as the left | same as the left | same as the left |
| reaction pressure (CO) Kg/cm$^2$ | 300 | | | | | | |
| reaction time hr | 1.5 | 1.5 | 1.5 | 1.5 | 1.5 | 1.5 | 1.5 |
| Reactivity of butadiene mole % | 97.7 | 97.8 | 97.3 | 98.0 | 96.8 | 98.5 | 99.1 |
| Yield of methyl 3-pentenoate mole % | 95.0 | 95.5 | 94.2 | 95.4 | 93.9 | 96.5 | 97.4 |
| Selectivity to methyl 3-pentenoate mole % | 97.2 | 97.6 | 96.9 | 97.4 | 97.0 | 98.0 | 98.3 |
| Selectivity to methyl 2 or 4 pentenoate mole % | 0.3 | 0.3 | 0.3 | 0.3 | 0.3 | 0.2 | 0.2 |
| Selectivity to 4-vinyl-1-cyclohexene mole % | 1.4 | 1.1 | 1.3 | 1.2 | 1.4 | 0.9 | 1.0 |
| Selectivity to dibutyl ketone mole % | 0.1 | 0.1 | 0.2 | 0.1 | 0.2 | 0.1 | 0.1 |
| Selectivity to dimethyl methylgultarate mole % | <0.1 | <0.1 | <0.1 | <0.1 | <0.1 | <0.1 | <0.1 |
| Selectivity to other unknown components containing polymers mole % | 0.9 | 0.8 | 1.2 | 0.9 | 1.0 | 0.7 | 0.3 |

What is claimed is:

1. In a process for producing a 3-pentenoic ester which comprises reacting butadiene, carbon monoxide and an alcohol in the presence of cobalt carbonyl catalyst and a solvent,
the improvement wherein the reaction is carried out in a reaction medium composed of at least two solvents selected from the group consisting of pyridine, quinoline, isoquinoline and substituted pyridine, substituted quinoline and substituted isoquinoline in which substituent or substituents are selected from the group consisting of alkyl having 1–6 carbon atoms, alkenyl having 1–6 carbon atoms, aryl, alkylaryl having 7–10 carbon atoms and aralkyl having 7–10 carbon atoms, and wherein any one of said at least two solvents is present in an amount of more than 2 moles % on the basis of total moles of the solvents.

2. The process as defined in claim 1 wherein the combined amount of at least two solvents is in the range of 0.05 to 10 parts by weight per part by weight of butadiene.

3. The process as defined in claim 1 wherein said reaction medium further contains at least one polymerization inhibitor selected from the group consisting of aromatic amino compounds, quinone compounds and aromatic hydroxy compounds (except hydroquinone).

4. The process as defined in claim 3 wherein the amount of polymerization inhibitor employed is in the range of more than 0.0001 mole per 1 mole of butadiene.

5. The process as defined in claim 1 wherein the cobalt carbonyl catalyst is dicobalt octacarbonyl.

6. The process as defined in claim 5 wherein dicobalt octacarbonyl is used in an amount ranging from 0.001 to 0.05 moles per 1 mole of butadiene.

7. The process as defined in claim 1 wherein the amount of the alcohol employed is more than 1 mole per mole of butadiene.

8. The process as defined in claim 1 wherein the reaction temperature is in the range of from 80° C. to 200° C.

9. The process as defined in claim 1 wherein partial pressure of carbon monoxide is more than 50 Kg/cm$^2$.

10. The process as defined in claim 1 wherein any one of said at least two solvents is present in an amount of more than 10 moles % on the basis of the total moles of solvent.

11. The process as defined in claim 1 wherein said cobalt carbonyl catalyst constitutes a synthetic solution obtained by reacting synthetic gas consisting essentially of carbon monoxide and hydrogen with at least one cobalt compound selected from the group consisting of inorganic and organic cobalt compounds in said alcohol; or a synthetic solution obtained by reacting at least one said cobalt compound, at least one of said at least two solvents, and CO gas.

* * * * *